(12) United States Patent
Darcey (10) Patent No.: US 6,261,252 B1
(45) Date of Patent: Jul. 17, 2001

(54) CUSTOM-MOLDABLE UNIVERSAL THUMB SPICA SPLINT

(75) Inventor: Thomas D. Darcey, Mooresville, NC (US)

(73) Assignee: Smith & Nephew, Inc., Charlotte, NC (US)

( * ) Notice: Subject to any disclaimer, the term of this patent is extended or adjusted under 35 U.S.C. 154(b) by 0 days.

(21) Appl. No.: 09/484,643

(22) Filed: Jan. 18, 2000

(51) Int. Cl.$^7$ ............................................. A61F 5/00
(52) U.S. Cl. ........................................... 602/6; 602/5
(58) Field of Search .............................. 602/5–10

(56) References Cited

U.S. PATENT DOCUMENTS

| | | |
|---|---|---|
| 4,382,439 | 5/1983 | Shen . |
| 4,524,464 | 6/1985 | Primiano et al. . |
| 4,683,877 | * 8/1987 | Ersfeld et al. . |
| 5,755,678 | * 5/1998 | Parker et al. . |
| 5,787,896 | * 8/1998 | Sackett . |

* cited by examiner

Primary Examiner—Michael A. Brown
Assistant Examiner—Lalita M. Hamilton

(74) Attorney, Agent, or Firm—Adams, Schwartz & Evans, P.A.

(57) ABSTRACT

A thumb spica splint for being custom-fitted to the thumb portion of the hand for immobilizing the thumb while permitting continued unrestricted use of the other fingers of the hand, and including an elongate, flexible inner cushion layer, an initially flexible intermediate layer overlying the inner cushion layer, the intermediate layer formed of a fabric impregnated or coated with a moisture-curable resin which hardens upon curing to form a rigid structure of the fabric which retains a shape into which it is molded during curing. A flexible protective outer layer overlies the intermediate layer and is attached to the inner cushion layer for enclosing the intermediate layer and forming the inner layer, intermediate layer and outer layer into a single, integrated splint structure. The splint is shaped to extend along and conform to the medial aspect of the lower arm and thumb to the distal joint thereof. An elongate thumb strap is fixedly attached by one end thereof to the splint structure adjacent the thumb for extending around the thumb and releasably attaching to a thumb strap attachment element fixedly attached to the splint structure for holding the splint structure in a supporting position around the thumb. Arm straps are fixedly attached by one end thereofto the splint structure adjacent the arm for extending around the arm and releasably attaching to an arm strap attachment element fixedly attached to the splint structure for holding the splint structure in a supporting position around the arm.

12 Claims, 11 Drawing Sheets

CUSTOM-MOLDABLE UNIVERSAL THUMB SPICA SPLINT

TECHNICAL FIELD AND BACKGROUND OF THE INVENTION

This invention relates to a custom-moldable universal thumb spica splint. The disclosure of this application includes a package in which a splint is contained for ease of sale, distribution and use. The splint according to the invention can be packaged and dispensed in single, moisture-proof packages or in any other suitable manner.

A thumb spica splint is indicated for immobilization of the proximal area of the thumb during healing of injury to the scaphoid bone of the hand. The spica splint immobilizes the proximal area of the thumb while permitting some movement of the distal end portion. The thumb is immobilized by holding it in alignment with the hand and wrist. Thumb spica splints are known, for example, U.S. Pat. No. 4,382,439; as well as safety gloves with a dorsal thumb spica brace, for example, U.S. Pat. No. 4,524,464.

Prior art splints often include a soft component to place near the skin and a hard, shell-like outer cover. The soft component is intended not only to provide a cushion, but also to accommodate itself to the varying configurations of differing sized and shaped hands.

Other splints are glove-like in design and are provided with bendable plastic or metal stays which are bent to position the hand and wrist in the desired position.

Some other prior art splints are constructed of or include thermosetting materials, which are heated and then formed to the hand and wrist while heated. These products require a source of heat, and are susceptible to either over-or-underheating. In addition, body heat itself can soften or at least increase the flexibility of the splint, thereby decreasing the effectiveness of the protection offered by the splint.

The present invention permits quick and easy application of a protective thumb spica splint to the hand in such a way as to achieve a true custom fit from a single design. The splint according to one embodiment is universal in the sense that it can be used on either the left or right hand.

The moisture curable resin system used results in a very rigid splint which holds the shape into which it is molded. No heat is required, and a source of water is the only additional material necessary to harden the splint. Atmospheric moisture alone will cure the splint into its hardened position in a relatively short period of time, but the resin in or on the splint will typically be activated by dipping in water. The splint is inexpensive, easy to fabricate, easy to fit and comfortable to wear. Since only one splint necessary, hospitals, clinics and other emergency care facilities can easily and inexpensively maintain a full inventory of splints without complications arising from the need to constantly monitor an inventory of different sizes and shapes.

SUMMARY OF THE INVENTION

Therefore, it is an object of the invention to provide a thumb spica splint which is a universal size and shape for either the left or right hand.

It is another object of the invention to provide a thumb spica splint which is easy to apply to the wrist, hand and thumb.

It is an object of the invention to provide a thumb spica splint which can be easily placed on and removed from the hand and wrist by the patient when necessary or desirable.

It is another object of the invention to provide a thumb spica splint which hardens in the presence of moisture to form a very rigid but very lightweight protective splint.

It is another object of the invention to provide a thumb spica splint which is stored in a moisture-proof pouch until ready for application to the body part to be protected.

These and other objects of the present invention are achieved in the preferred embodiments disclosed below by providing a thumb spica splint for being custom-fitted to the thumb portion of the hand for immobilizing the thumb while permitting continued unrestricted use of the other fingers of the hand, and comprising an elongate, flexible inner cushion layer, an initially flexible intermediate layer overlying the inner cushion layer, the intermediate layer comprised of a fabric impregnated or coated with a moisture-curable resin which hardens upon curing to form a rigid structure of the fabric which retains a shape into which it is molded during curing, thereby also holding the flexible inner cushion layer in a conforming shape around the thumb. A flexible protective outer layer overlies the intermediate layer and is attached to the inner cushion layer for enclosing the intermediate layer and forming the inner layer, intermediate layer and outer layer into a single, integrated splint structure. The integrated splint structure is shaped to extend along and conform to the medial aspect of the lower arm and thumb to the distal joint thereof. Thumb strap means comprising an elongate thumb strap are fixedly attached by one end thereof to the splint structure adjacent the thumb for extending around the thumb and releasably attaching to a thumb strap attachment means fixedly attached to the splint structure for holding the splint structure in a supporting position around the thumb. Arm strap means comprising an elongate arm strap are fixedly attached by one end thereof to the splint structure adjacent the arm for extending around the arm and releasably attach to an arm strap attachment means fixedly attached to the splint structure for holding the splint structure in a supporting position around the arm.

According to one preferred embodiment of the invention, the fabric comprises a plurality of overlaid thicknesses of fiberglass.

According to another preferred embodiment of the invention, the plurality of thicknesses of fiberglass comprises at least five thicknesses and no more than seven thicknesses.

According to yet another preferred embodiment of the invention, the thumb attachment strap and the thumb strap attachment means comprise one or the other of male and female touch fastener elements.

According to yet another preferred embodiment of the invention, the arm attachment strap and the arm strap attachment means comprise one or the other of male and female touch fastener elements.

According to yet another preferred embodiment of the invention, an arm attachment strap is fixedly attached to the splint structure at an angle whereby the strap extends spirally around the arm, and the arm strap attachment means is attached to the splint structure in a longitudinally-offset position to receive and releasably mate with the spirally-extended attachment strap.

According to yet another preferred embodiment of the invention, the cushion layer comprises EVA closed cell foam.

According to yet another preferred embodiment of the invention, the splint includes a notch formed in the splint and positioned to reside over the thumbnail for permitting greater flexibility of the splint when being formed around the circumference of the thumb and for permitting observation of the degree of capillary refill when determining whether the splint has been applied with the proper degree of tightness.

According to yet another preferred embodiment of the invention, the invention includes a moisture-proofpouch in which the splint is contained in a flexible condition in moisture-free conditions until being opened immediately prior to application to the arm and thumb.

According to yet another preferred embodiment of the invention, the outer moisture-proofprotective pouch is formed of a laminated structure having at least one layer of plastic film and at least one layer of aluminum foil bonded to the plastic film.

According to yet another preferred embodiment ofthe invention, a thumb spica splint is provided for being custom-fitted to the thumb portion of the hand for immobilizing the thumb while permitting continued unrestricted use of the other fingers of the hand, and comprises an elongate, flexible inner cushion layer, an initially flexible intermediate layer overlying the inner cushion layer, the intermediate layer comprised of a fabric impregnated with a moisture-curable resin which hardens upon curing to form a rigid structure of the fabric which retains a shape into which it is molded during curing, thereby also holding the flexible inner cushion layer in a conforming shape around the thumb, and a flexible protective outer layer overlying the intermediate layer and attached to the inner cushion layer for enclosing the intermediate layer and forming the inner layer, intermediate layer and outer layer into a single, integrated splint structure. The integrated splint structure is shaped to extend along and conform to the medial aspect of the lower arm and thumb to the distaljoint thereof. Thumb strap means comprising an elongate thumb strap are fixedly attached by one end thereof to the splint structure adjacent the thumb for extending around the thumb and releasably attaching to a thumb strap attachment means fixedly attached to the splint structure for holding the splint structure in a supporting position around the thumb. Arm strap means comprising first and second elongate arm straps are provided for being attached by one end thereof to the splint structure adjacent the arm for extending spirally around the arm in opposite directions and releasably attaching to respective first and second arm strap attachment means attached to the splint structure in respective longitudinally-offset positions for mating with the spirally-extended arm straps holding the splint structure in a supporting position around the arm.

According to yet another preferred embodiment ofthe invention, first and second arm straps spirally extend around the arm in the same longitudinal direction and thereby criss-cross on the side of the arm opposite the splint.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
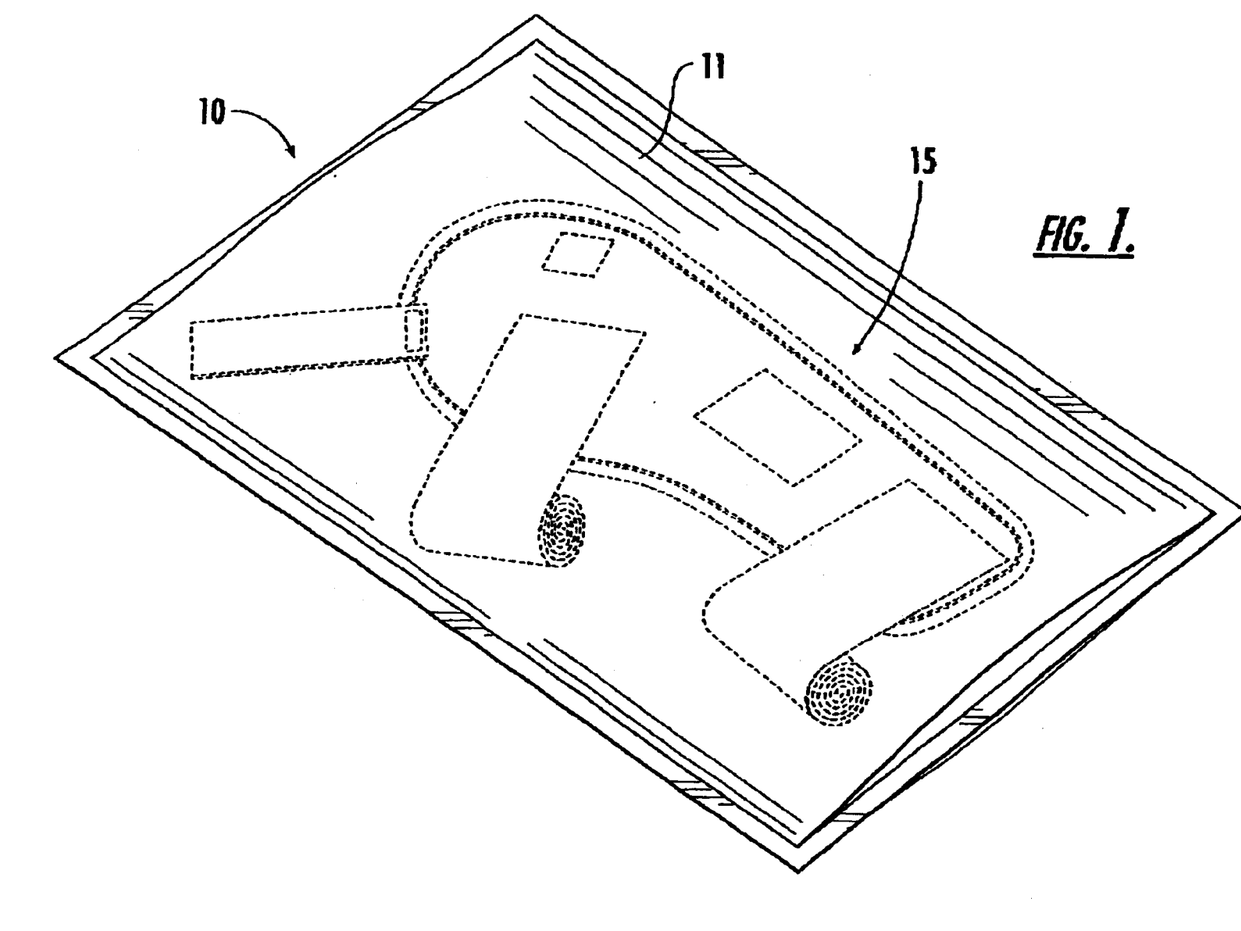
FIG. 1 is a view of a thumb spica splint assembly, including the moisture-proof outer storage container and the splint stored therein.

Referring now specifically to the drawings, FIG. 1 illustrates a splint assembly 10 according to an embodiment of the invention. The splint assembly 10 includes as its outermost protective enclosure an outer moisture-impervious foil and laminated pouch 11 in which the splint according to the disclosure of this application is sealed in the absence of moisture. The preferred structure of the outer moisture-impervious pouch 11 include a 0.5 mil aluminum foil sheet sandwiched between two layers of low density polyethylene film each layer having a thickness of 2 mils. Additionally, the pouch 11 can include an outer layer of laminated 60 gauge bi-axially oriented nylon film. This laminate structure, when properly sealer will prevent moisture intrusion indefinitely. A thumb spica splint 15 according to one preferred embodiment of the invention is shown within the pouch 11.

Figure 2:
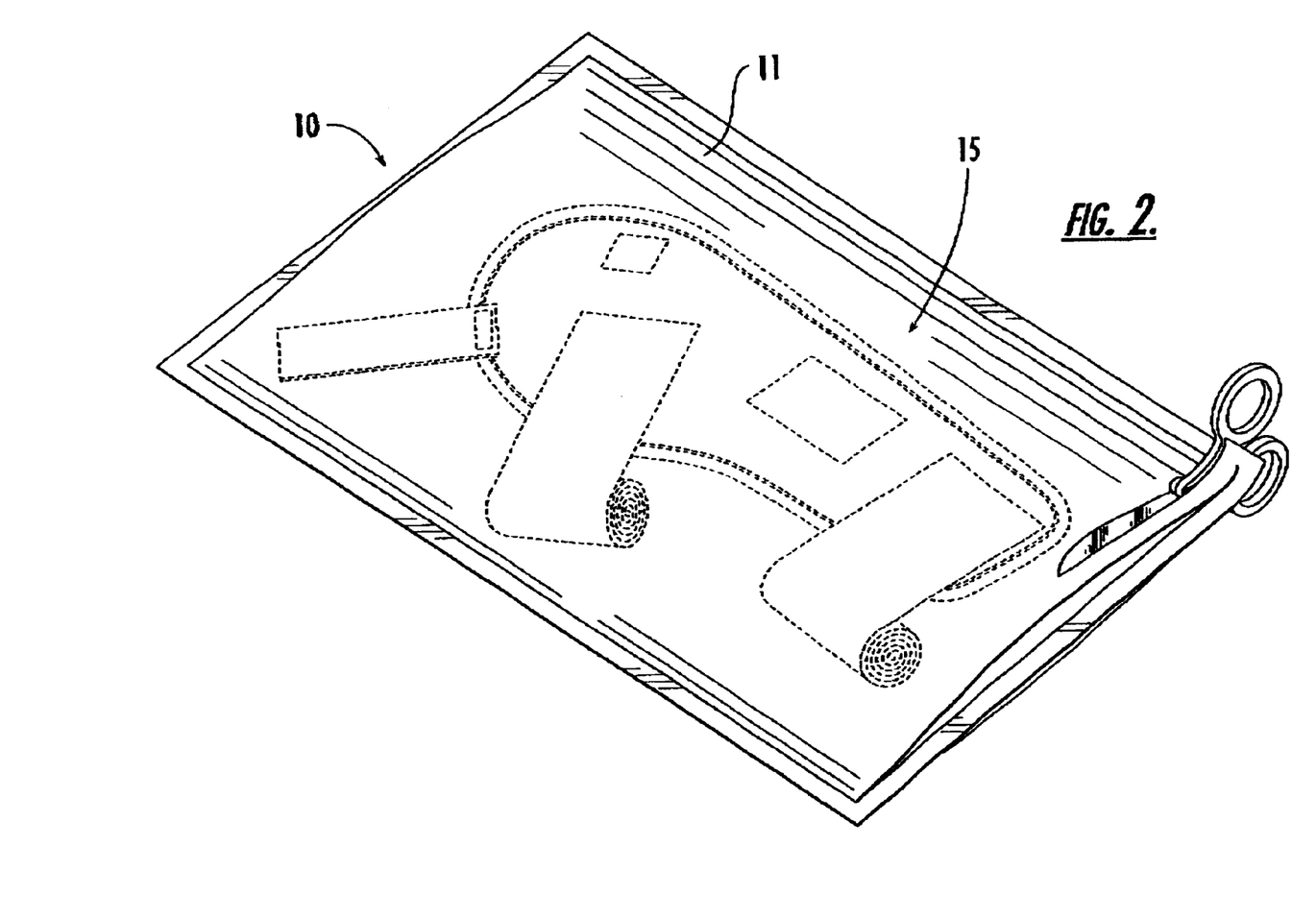
FIG. 2 is a view showing removal of the splint immediately prior to use.

The moisture-impervious foil and plastic laminated pouch 11 is opened with scissors or a knife, as shown in FIG. 2, and the splint 15 is removed.

Figure 3:
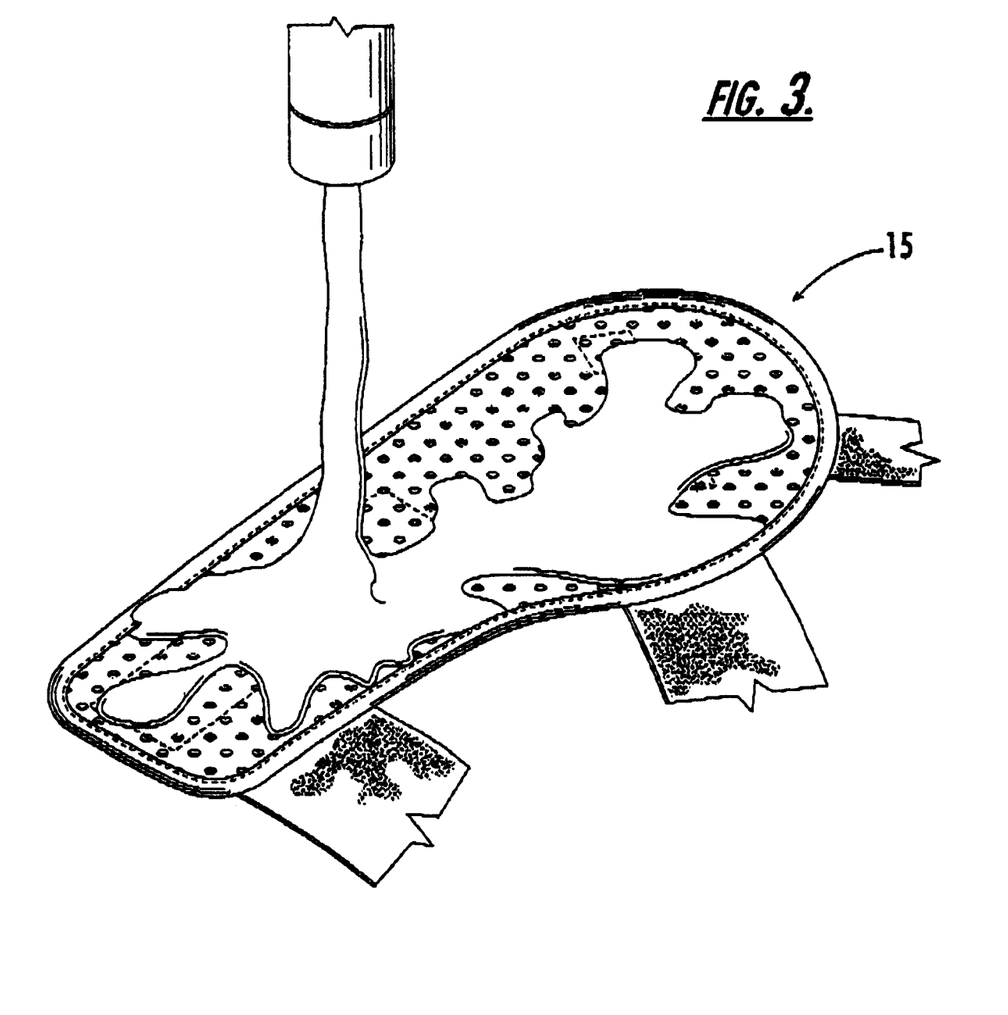
FIG. 3 illustrates wetting the splint immediately prior to application to the injured hand.

As is shown in FIG. 3, the splint 15 is wetted with water, for example, by holding it under a tap, as shown, or by immersion, to activate the moisture-curable resin with which the splint 15 is impregnated or coated. The wet splint 15 is then applied to the injured limb. The splint 15 will harden within a matter of minutes, and will retain the conformation in which it was held during curing. The splint 15 is preferably held in place during curing with an elastic bandage to supplement the straps which are a part of the splint 15, as described below. Preferably, such a bandage is supplied with the splint assembly 10.

Figure 4:
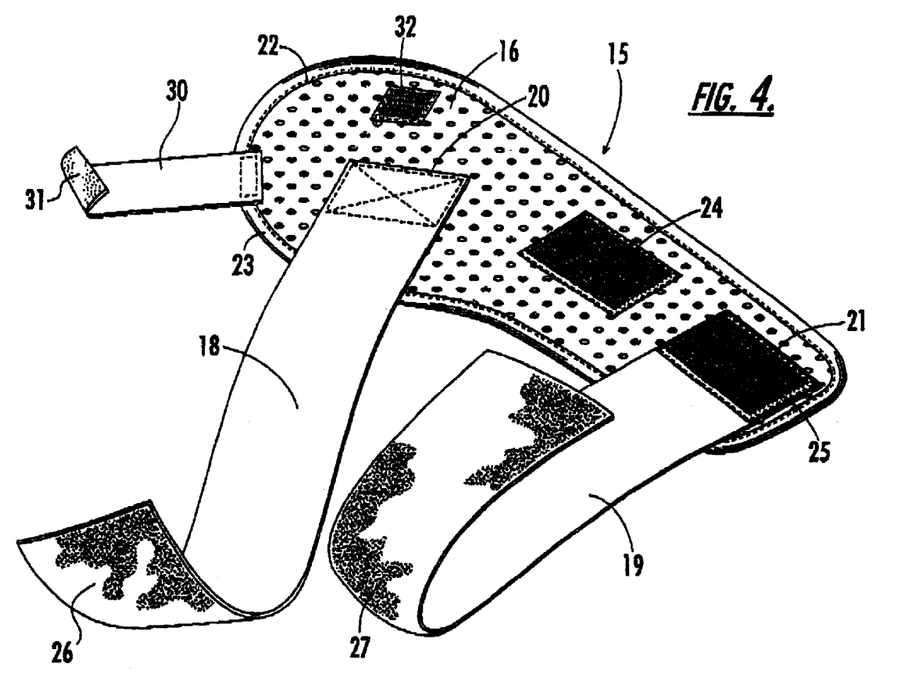
FIG. 4 is a plan view of a splint according to one embodiment of the invention.

Referring now to FIG. 4, the outer surface of the splint 15 is generally shown, and includes a flexible protective outer layer 16 of relatively open polyester sheeting. The splint 15 is held around the lower arm and hand by a pair of straps 18 and 19 fastened by sewing stitches 20 and 21 through the entire thickness of the splint 15. The overall shape of the splint 15 is symmetrical from left-to-right, but slightly wider on the end distal end which will receive the thumb. This permits the same splint 15 to be used on either the left or right hand. The term "symmetrical" as used herein contemplates some difference in shape from one side o the other, so long as it is not so great as to prevent use on either the left or the right hand.

Respective patches of hook material 24 and 25 releasably interconnect with loops of continuous filament fibers 26, 27 on the inner side ofthe straps 18, 19. This type of male and female material is known as "hook-and-loop" fasteners or "touch" fasteners. Of course, of forms of fasteners can be used, such as buckle or D-ring straps, or straps which are completely separate from the splint structure and which include both hook and loop material, buckles, D-rings or other fastener mechanisms for permitting the strap to be secured around the splint.

In addition, the entire outer surface ofthe splint 15 can be covered with fabric having loop material on the outer surface, so that straps with one or more patches of cooperating hooks will interconnect. The advantages in using hook-and-loop mate rial include easy fastening and unfastening, an infinite adjustment within the total range of adjustment, and the ability to launder the entire splint 15, including the fasteners.

The thumb of the injured limb is immobilized by means of a strap 30 with loops 31 which extends around the base of the thumb and attaches to a patch of hook material 32.

Figure 5:
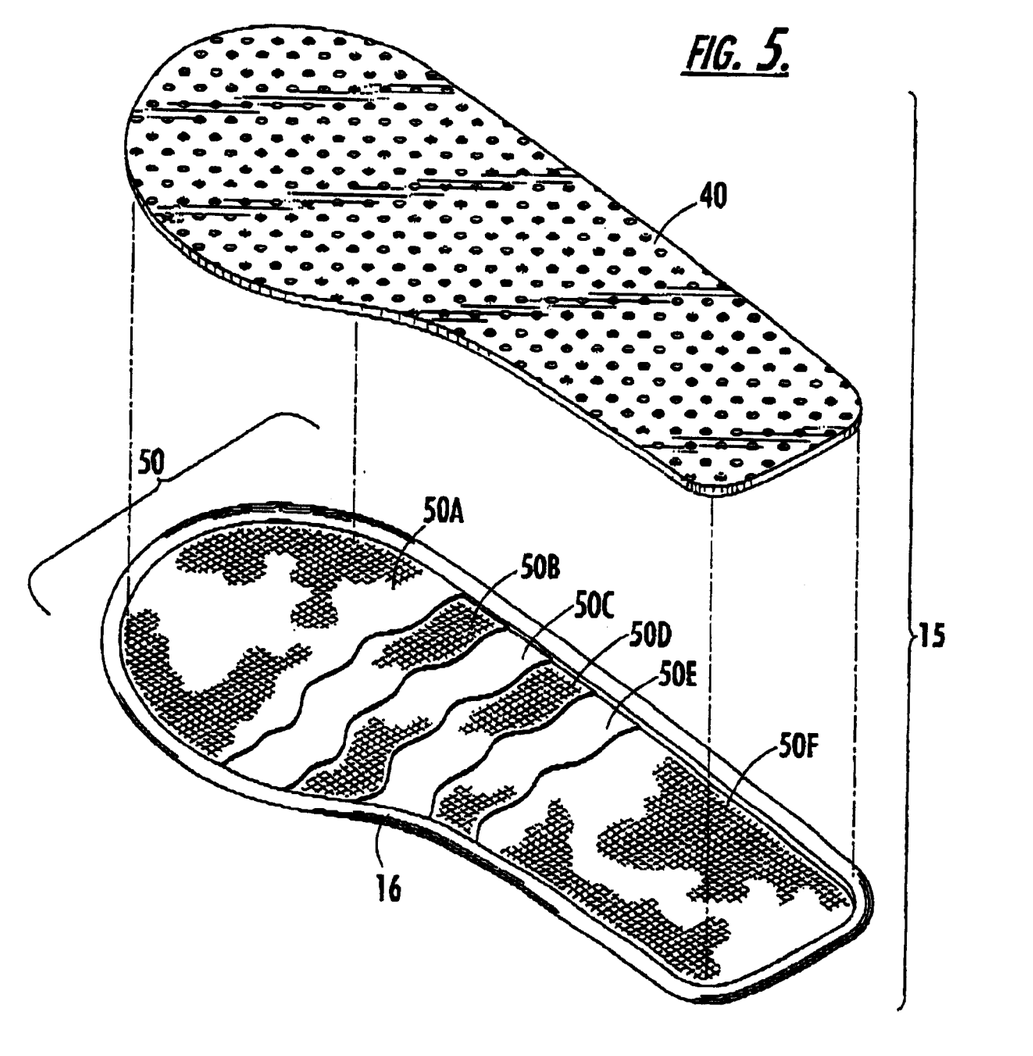
FIG. 5 is a fragmentary exploded view of the splint from the side reverse from FIG. 4, with straps omitted for clarity.

Referring now to FIG. 5, the layers of splint 15 are illustrated and described more specifically.

The outer fabric layer 16 forms the outer surface of the splint 15 and a flexible inner cushion layer 40 is provided for being placed closest to the hand. Inner cushion layer 40 is preferably a laminated one-eighth inch, four pound EVA (ethylen vinyl acetate) micro-perf closed cell foam. The cushioning provides a comfortable surface next to the skin. The EVA is flexible enough to bend easily with the other components of the splint 15. The fabric outer layer 16 and the inner cushion layer 40 are joined around the perimeter by overedge sewing stitches 22 which capture a narrow seam-binding tape 23.

An initially flexible intermediate layer 50 is sandwiched between the outer fabric layer 16 and the inner foam cushion layer 20. The intermediate layer 50 is preferably formed of six fiberglass fabric layers 50A–F impregnated with a moisture-curable resin which hardens upon curing to form a rigid structure which retains shape of the hand and wrist onto which it is molded prior to curing. As noted, the particular embodiment illustrated in this application contains six layers of E-fiberglass fabric, but other variations are suitable. For example, the fiberglass may be S-fiberglass. S-fiberglass has a is 30 percent stronger, 15 percent stiffer and significantly tougher than typical E-fiberglass. One particular suitable S-fiberglass is a single thickness 6580 plain weave industrial fiberglass fabric made by Clark-Schwebel. Other fiberglass constructions may be suitable, including other woven constructions and knitted constructions. Type 6580 S-fiberglass fabric has 73 warp ends and 70 filling ppi, a weight of 5.58 oz/yd$^2$ and a breaking strength of 147 lbs/in (warp) and 145 lbs/in (filling). Type 6580 S-fiberglass fabric is 0.0063 inches thick. Type 6580 S-fiberglass has an ultimate tensile strength of 37.9 ksi and an elastic modulus of 2026.8. These characteristics make this particular fiberglass an ideal choice.

Other fabrics which may be suitable for the sheets include fabrics made of a composition of aluminum oxide, silicone oxide and boron oxide and sold under the trademark Nextel 440 by Thermostatic Industries, Inc.; silica-based fabrics, high modulus fabrics sold under the DuPont trademark "Kevlar."

An alternative to the use of multiple layers of fabric is a single thickness sheet of random laid non-continuous polyester nonwoven fabric incorporating a styrene-soluble binder filled 60 percent by volume with plastic microspheres. The product is sold under the trademark "Firet Coremat XM by Baltek. This product is available in 2 mm, 3 mm and 4 mm thicknesses. The 2 mm thickness has been found suitable, and weighs 2.7–3.2 oz/yd$^2$, has a cured specific gravity of 31.0–37.0 lb/ft$^3$, and a resin consumption of 3.1–3.3 oz/ft$^3$.

Other Firet Coremat grades, such as Firet Coremat XX and Firet Coremat XW may also be suitable. These grades are filled with plastic microsphere to 50 percent by volume. Other products which may be suitable include a low density, nonwoven continuous strand fabric such as BaltekMat T-2000. This product has characteristics which are generally similar to Firet Coremat, but is generally unavailable in small quantities.

The fiberglass fabric layers 50A–F or other substrate materials are impregnated or coated with a moisture-curable resin such as polyisocyanate as described in full in the present applicant's U.S. Pat. No. 4,770,299. This reactive system remains stable when maintained in substantially moisture-free conditions, such as in the moisture-impervious pouch 11, but hardens upon exposure to sufficient moisture to form a rigid, self-supporting structure. A typical formulation of the reaction system is set forth in the following table:

| Typical Formulation: | | |
|---|---|---|
| Isonate ↓ 153L | or | |
| Mondur ↓ CD | or polyisocyanate | 50.0% |
| Rubinate ↓ XI168 | | |
| Pluracol ↓ P1010 | polvol | 46.6% |
| DC-200 Silicone | defoaming agent | 0.30% |
| Benzoyl Chloride | stabilizer | 0.10% |
| Thancat DM-70 | catalyst | 3.0% |
| | | 100% |

A complete discussion of the parameters of the reactive system, the manner of production and the variables which apply are found in U.S. Pat. No. 4,411,262.

The polyisocyanate resin remains in a viscous, liquid unhardened state so long as the resin is not exposed to moisture. This permits the fiberglass intermediate layers 50 and any flexible structure, such as the inner cushion layer 40, to remain flexible and moldable so long as the resin is not exposed to moisture, and for a relatively short period of time after exposure to moisture.

The curing time can be controlled to some extent by the quantity of water to which the resin is exposed. For example, exposure to water by dipping will result in quite rapid curing, while merely allowing the resin to be exposed to air will cause long curing times proportional to the amount of humidity in the air to which it is exposed.

In accordance with the invention, the individual fiberglass fabric layers 50A–F are preferably die-cut to shape. The various fabric layers 50A–F may have the same or different widths, and the degree of overlap and non-overlap resulting from the differing widths has the effect of providing variable thickness with a relatively thick predetermined area where increased rigidity is desirable and a relatively thin area where increased flexibility is desirable. The manner varying the widths of the fabric layers 50A–F is described in detail in prior U.S. Pat. No. 5,755,678. Preferably, each of the fiberglass fabric layers 50A–F are the same length and width. The individual fiberglass fabric layers 50A–F can also be formed by computer-controlled knitting whereby the shaped knitted structures are formed during the knitting process into the proper shape, thus relieving otherwise sharp, cut edges and simplifying the assembly of the splint 15.

Alternatively, some of the layers 50A–F may be of other material, such as polypropylene, which offers additional flexibility and some cost savings in material.

Figure 6:
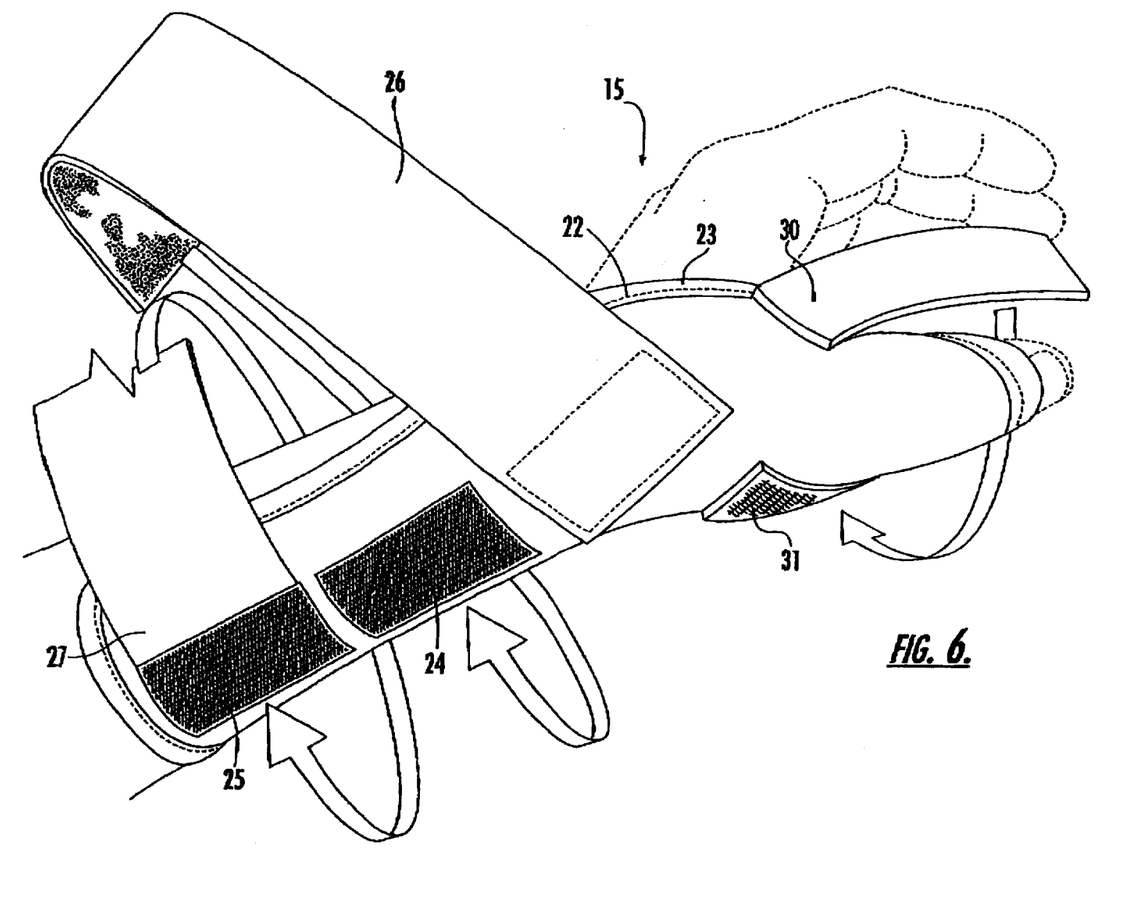
FIG. 6 is a view showing application of the splint to the arm.
Figure 7:
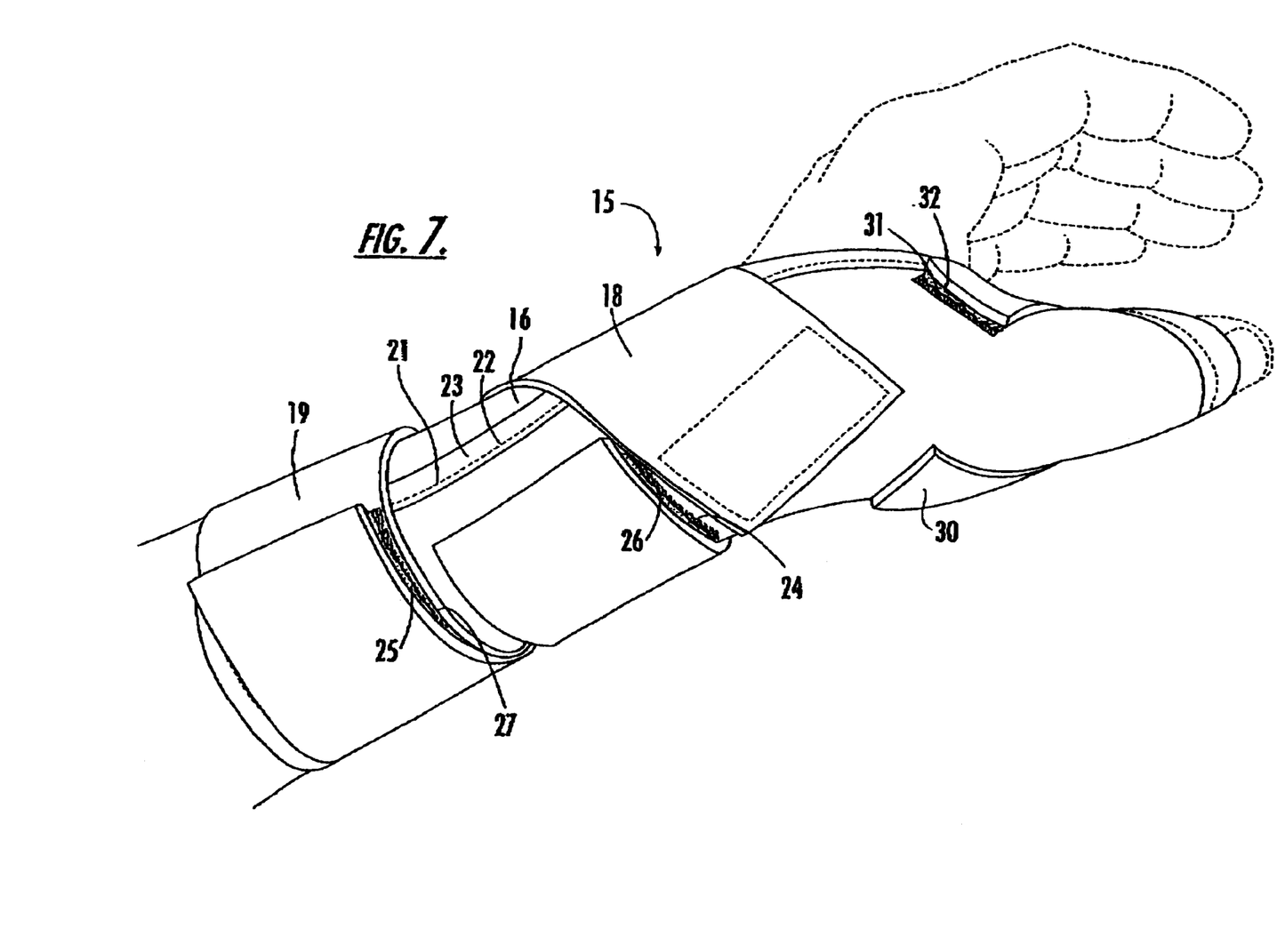
FIG. 7 is a view of the splint applied to the hand.

Referring now to FIG. 6, the splint 15 is applied to the hand and wrist with the straps 18, 19 and 30, as described above. The strap 19 extends radially around the circumference of the lower forearm or wrist. The strap 18 extends both radially and axially around the wrist in a spiral manner and thus provides support along a greater axial length without requiring more or wider straps. Properly applied, all but the last joint of the thumb is covered by the splint 15, with the strap 15 holding the overlaid layers 16, 40 and 50 around the base of the thumb, as shown in FIG. 7.

One preferred embodiment of the splint 15 has the following specifications:

| | |
|---|---|
| Overall length | 9.5 in. |
| Overall width | 4.65 in. |
| Strap 18 | 2 in. wide by 11 in. long |
| Strap 19 | 2 in. wide by 12 in. long |
| Strap 39 | 1 in. wide by 4 in. long |
| Outer layer 16 | Polyester sheeting |
| Inner layer 40 | .125 inch microperf EVA closed cell foam |
| Width of fiberglass intermediate layers 50 | 4 in. at distal end 3 in. at proximal end |
| Length of fiberglass intermediate layers 50 | 7.75 in. |
| Number of fiber glass layers | 6 |

Figure 8:
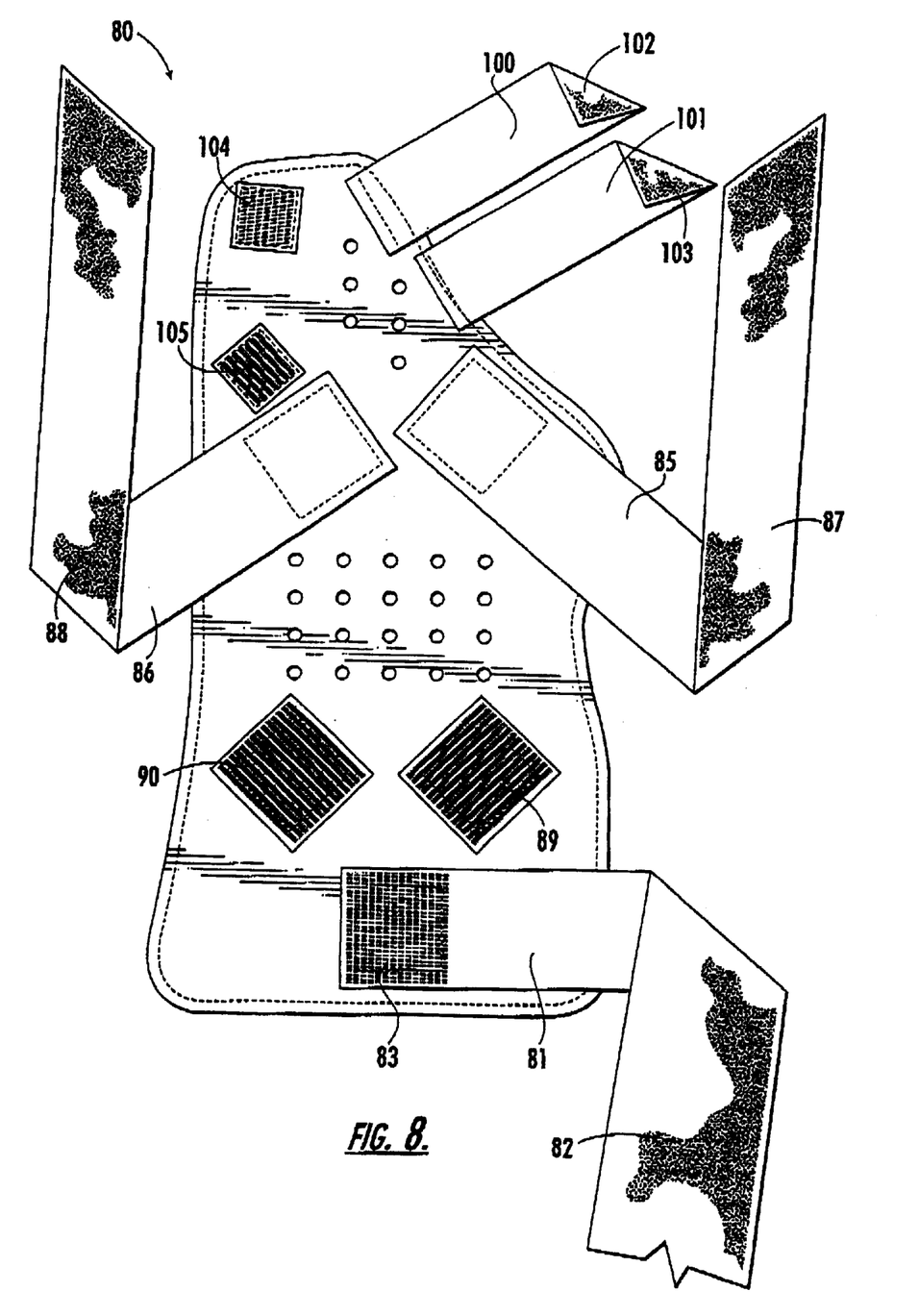
FIG. 8 is a plan view of the outer side of a thumb spica splint according to an alternative embodiment of the invention.
Figure 9:
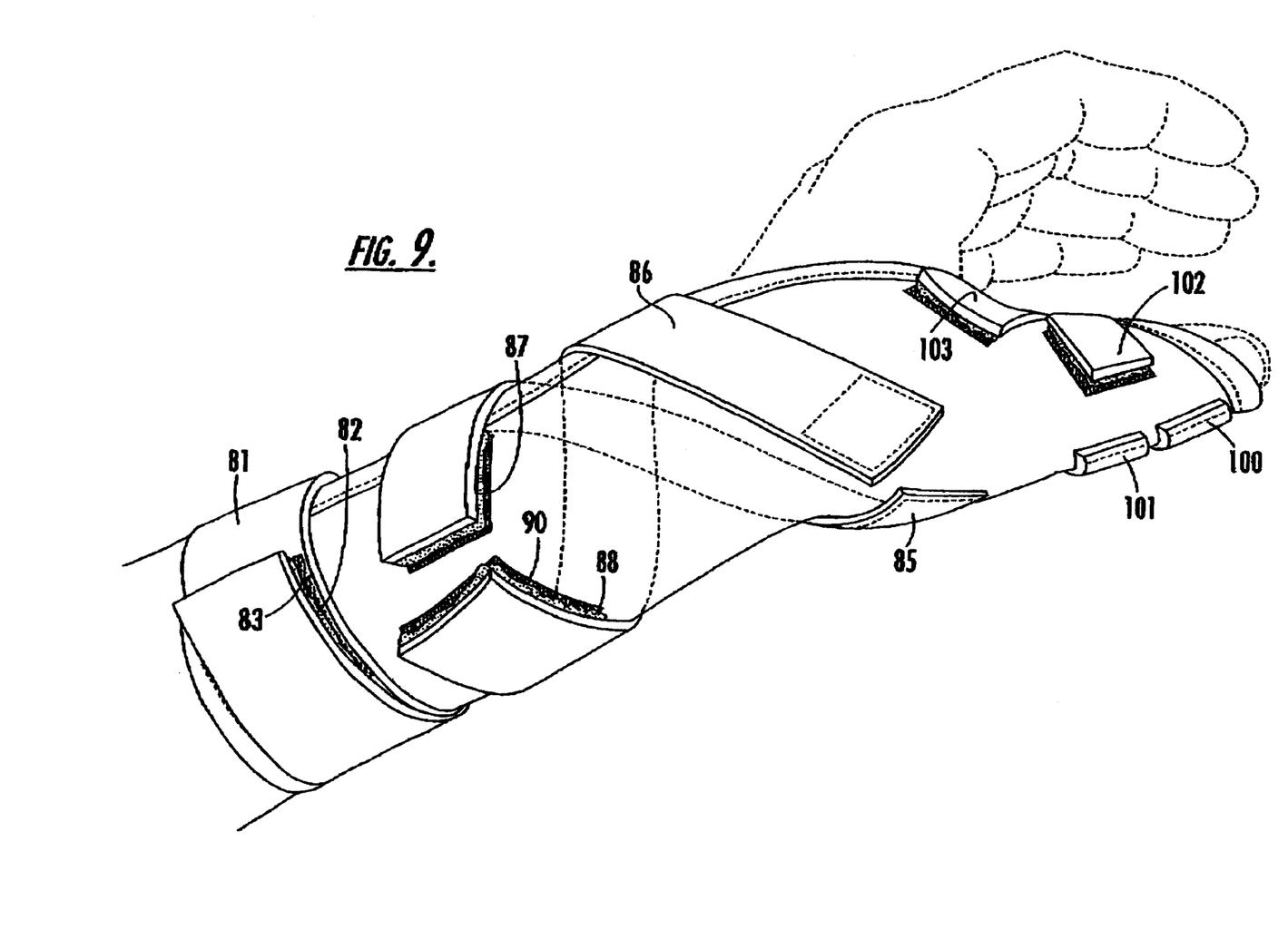
FIG. 9 is a view of the splint of FIG. 8 applied to the hand.

An alternative embodiment of a thumb spica splint according to the invention is illustrated in FIGS. 8 and 9 and broadly indicated at 80. The overall structure of the splint 80, including the materials from which the outer, inner and intermediate layers are constructed, is the same as described above except for the arrangement of the straps. Thus, the above disclosure is incorporated herein by reference. The splint 80, as shown, is for a right hand. The left-handed splint would be identical in structure but a mirror image. The splint 80 can also be made in a left-or-right universal shape just as the splint 15 disclosed above.

The splint 80 includes a strap 81 which has loops 82 on its inner surface and extends radially around the forearm and attaches to a patch of mating hooks 83 secured to the outer surface of the splint 80.

A pair of straps 85 and 86 with respective loops 87 and 88 are attached so as to extend both radially and axially around the wrist and attach to respective patches of hooks 89 and 90 in a spiral, criss-cross manner, as shown in FIG. 8.

The thumb itself is immobilized by a pair of straps 100, 101 which include respective loops 102, 103 and extend around the thumb and attach to respective patches of hooks 104 and 105.

The splint 80 in place on the injured limb is shown in FIG. 9, and as with splint 15 covers all but the last joint of the thumb.

One preferred embodiment of the splint 80 has the following specifications:

| | |
|---|---|
| Overall length | 9.5 in. |
| Overall width | 4.65 in. |
| Strap 81 | 2 in. wide by 11 in. long |
| Straps 85 and 86 | 2 in. wide by 12 in. long |
| Straps 100 and 103 | 1 in. wide by 4 in. long |
| Outer layer | Polyester sheeting |
| Inner layer | .125 inch microperf EVA closed cell foam |
| Width of fiberglass intermediate layers | 1 in. |
| Length of fiberglass intermediate layers | 7.75 in. |
| Number of fiberglass layers | 6 |

Figure 10:
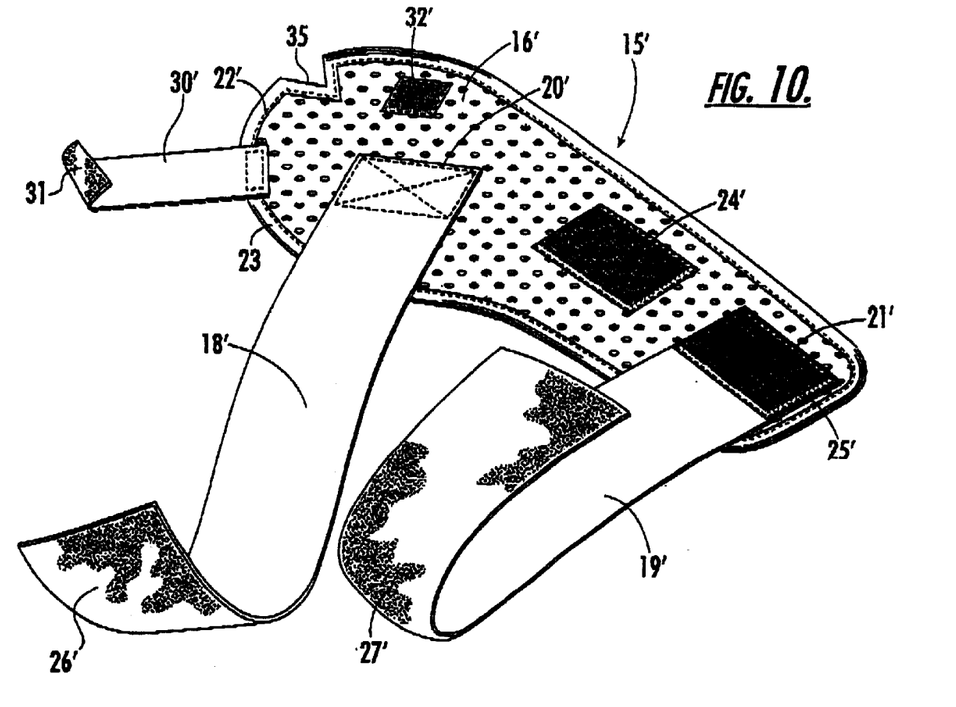
FIG. 10 is a plan view of an alternative embodiment including a notch over the thumbnail.
Figure 11:
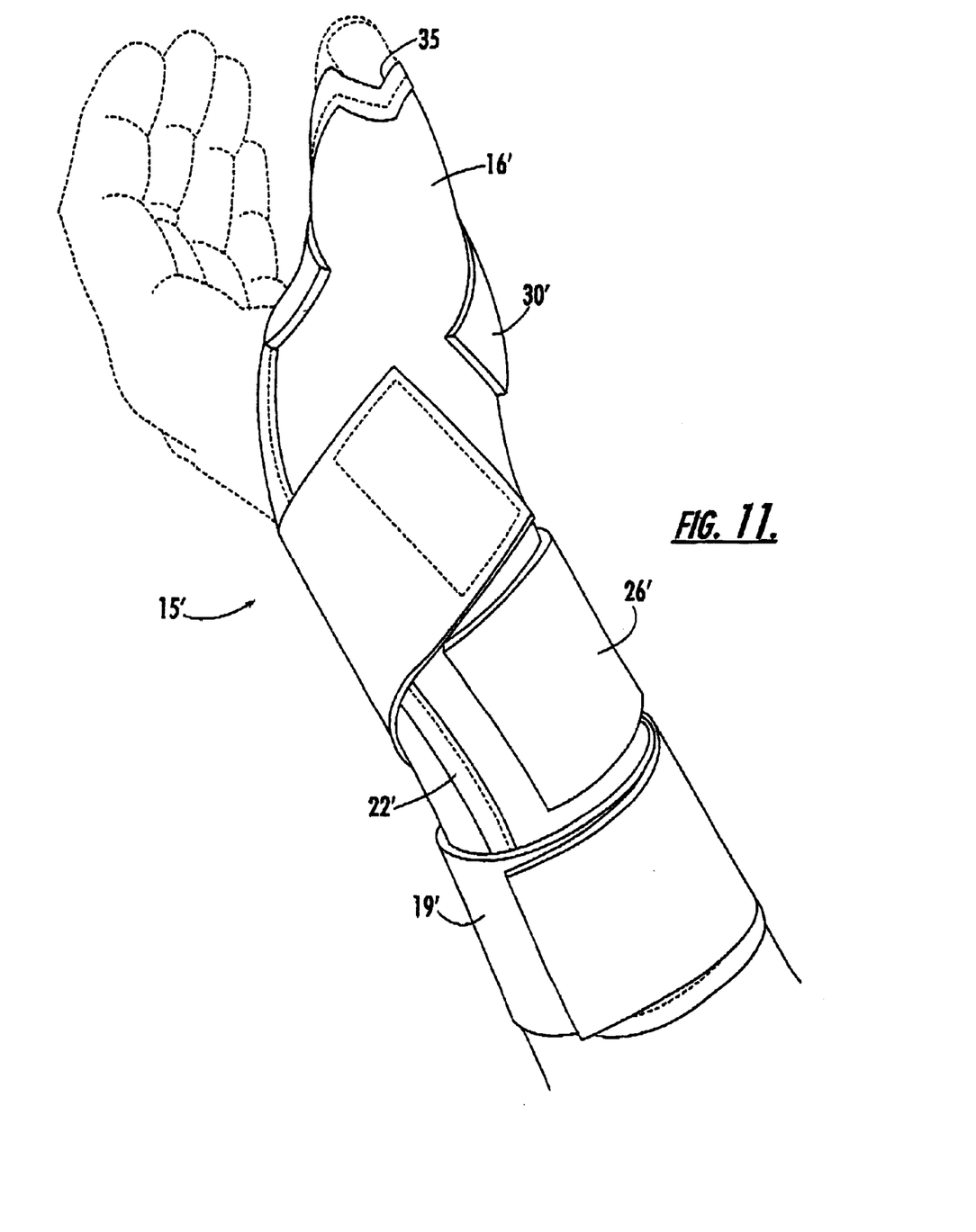
FIG. 11 is a view of the splint in FIG. 10 applied to the hand.

As is shown in FIGS. 10 and 11, a splint 15' is shown and includes a small V- or U-shaped notch 35 formed in the distal end of the splint 15 and positioned to reside directly over the exposed thumbnail when the splint is applied to the hand. The notch 35 permits the splint 15 to be folded more sharply around the thumb and thereby contact more of its circumference. In addition, by exposing more of the thumbnail, it is more easily determined that the splint has not been applied too tightly. This is accomplished by blanching the thumbnail by pressing it, and observing the degree of capillary refill. Splint 15' is otherwise identical to splint 15 and thus the prime notation applied to the reference numerals in FIGS. 10 and 11 correlate to the identical elements in FIGS. 1–7.

While not shown, the notch as described above can also be applied to the splint 80 shown in FIGS. 8 and 9.

A universal thumb spica splint is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A thumb spica splint for being custom-fitted to the thumb portion of the hand for immobilizing the thumb while permitting continued unrestricted use of the other fingers of the hand, and comprising:

(a) an elongate, flexible inner cushion layer;

(b) an initially flexible intermediate layer overlying the inner cushion layer, said intermediate layer comprised of a fabric impregnated with a moisture-curable resin which hardens upon curing to form a rigid structure of the fabric which retains a shape into which it is molded during curing, thereby also holding the flexible inner cushion layer in a conforming shape around the thumb;

(c) a flexible protective outer layer overlying the intermediate layer and attached to the inner cushion layer for enclosing the intermediate layer and forming the inner layer, intermediate layer and outer layer into a single, integrated splint structure;

(d) the integrated splint structure shaped to extend along and conform only to the medial aspect of the lower arm and thumb to the distal joint thereof while leaving the lateral aspect of the lower arm uncovered to promote ventilation to the arm and blood circulation within the arm;

(e) an elongate thumb strap fixedly attached by one end thereof to the splint structure adjacent the thumb for extending around the thumb and releasably attaching to a thumb strap attachment member fixedly attached to the splint structure for holding the splint structure in a supporting position around the thumb; and (f) at least one arm strap fixedly attached by one end thereof to the splint structure adjacent the arm for extending around the arm and releasably attaching to an arm strap attachment means member attached to the splint structure for holding the splint structure in a supporting position around the arm.

2. A thumb spica splint according to claim 1, wherein said fabric comprises a plurality of overlaid thicknesses of fiberglass.

3. A thumb spica splint according to claim 2, wherein said plurality of thicknesses of fiberglass comprises at least five thicknesses and no more than seven thicknesses.

4. A thumb spica splint according to claim 2, wherein said thumb attachment strap and said thumb strap attachment member comprise one or the other of male and female touch fastener elements.

5. A thumb spica splint according to claim 2, wherein said arm attachment strap and said arm strap attachment members comprise one or the other of male and female touch fastener elements.

6. A thumb spica splint according to claim 5, wherein said arm attachment strap is fixedly attached to the splint structure at an angle whereby the strap extends spirally around the arm, and said arm strap attachment member is attached to the splint structure in a longitudinally-offset position to receive and releasably mate with the spirally-extended attachment strap.

7. A thumb spica splint according to claim 1, wherein said splint structure is generally symmetrical on either side of a longitudinal axis for permitting use of the splint on either the left or the right hand.

8. A thumb spica splint according to claim 1, and including a notch formed in the splint and positioned to reside over the thumbnail for permitting greater flexibility of the splint when being formed around the circumference of the thumb and for permitting observation of the degree of capillary refill when determining whether the splint has been applied with the proper degree of tightness.

9. A thumb spica splint according to claim 1, 2, 3, 4, 5, 6, 7 or 8, and including a moisture-proof pouch in which the splint is contained in a flexible condition in moisture-free conditions until being opened immediately prior to application to the arm and thumb.

10. A carpal tunnel splint assembly according to claim 9, wherein said outer moisture-proof protective pouch is formed of a laminated structure having at least one layer of plastic film and at least one layer of aluminum foil bonded to the plastic film.

11. A thumb spica splint for being custom-fitted to the thumb portion of the hand for immobilizing the thumb while permitting continued unrestricted use of the other fingers of the hand and comprising:

(a) an elongate, flexible inner cushion layer;

(b) an initially flexible intermediate layer overlying the inner cushion layer, said intermediate layer comprised of a fabric impregnated with a moisture-curable resin which hardens upon curing to form a rigid structure of the fabric which retains a shape into which it is molded during curing, thereby also holding the flexible inner cushion layer in a conforming shape around the thumb;

(c) a flexible protective outer layer overlying the intermediate layer and attached to the inner cushion layer for enclosing the intermediate layer and forming the inner layer, intermediate layer and outer layer into a single, integrated splint structure;

(d) the integrated splint structure shaped to extend along and conform only to the medial aspect of the lower arm and thumb to the distal joint thereof while leaving the lateral aspect of the lower arm uncovered to promote ventilation to the arm and blood circulation within the arm;

(e) an elongate thumb strap fixedly attached by one end thereof to the splint structure adjacent the thumb for extending around the thumb and releasably attaching to a thumb strap attachment fixedly attached to the splint structure for holding the splint structure in a supporting position around the thumb; and (f) first and second elongate arm straps for being attached by one end thereofto the splint structure adjacent the arm for extending spirally around the arm in opposite directions and releasably attaching to respective first and second arm strap attachment members attached to the splint structure in respective longitudinally-offset positions for mating with the spirally-extended arm straps holding the splint structure in a supporting position around the arm.

12. A thumb spica splint according to claim 11, wherein said first and second arm straps spirally extend around the arm in the same longitudinal direction and thereby criss-cross on the side of the arm opposite the splint.

\* \* \* \* \*